US010595767B2

(12) United States Patent
Shin et al.

(10) Patent No.: US 10,595,767 B2
(45) Date of Patent: Mar. 24, 2020

(54) APPARATUS AND METHOD FOR RECOGNIZING SYMPTOMS OF DEMENTIA AND PROVIDING DEMENTIA PATIENT MANAGEMENT SERVICE

(71) Applicant: Electronics and Telecommunications Research Institute, Daejeon (KR)

(72) Inventors: Hyun-Soon Shin, Daejeon (KR); Seung-Yoon Nam, Busan (KR); Seok-Hee Lee, Cheongju-si (KR); Chan-Young Hahm, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 332 days.

(21) Appl. No.: 15/269,312

(22) Filed: Sep. 19, 2016

(65) Prior Publication Data
US 2017/0095193 A1    Apr. 6, 2017

(30) Foreign Application Priority Data
Oct. 5, 2015    (KR) .......................... 10-2015-0139696

(51) Int. Cl.
*G16H 10/60*    (2018.01)
*A61B 5/11*    (2006.01)
*A61B 5/00*    (2006.01)

(52) U.S. Cl.
CPC .......... *A61B 5/4088* (2013.01); *A61B 5/1118* (2013.01); *A61B 5/1123* (2013.01);
(Continued)

(58) Field of Classification Search
CPC .......... G06F 19/30; G09B 5/02; A61B 5/4008; A61B 5/1118; A61B 5/1123;
(Continued)

(56) References Cited

U.S. PATENT DOCUMENTS 6,747,561 B1 *  6/2004  Reeves .................. G06F 1/1626
340/573.1
9,257,029 B1 *  2/2016  Hendrick, III ..... G08B 21/0415
(Continued)

FOREIGN PATENT DOCUMENTS

KR    1020100026302 A    3/2010

*Primary Examiner* — Xuan M Thai
*Assistant Examiner* — Malina D. Blaise
(74) *Attorney, Agent, or Firm* — William Park & Associates Ltd.

(57) ABSTRACT

Disclosed are an apparatus and method for detecting dementia and providing a dementia patient management service. A dementia symptom recognition apparatus includes a reception unit for receiving physiological signals of a dementia patient collected by sensors corresponding to a dementia detection device, an ambient environmental information signal, a location signal, a motion signal, an audio signal, and a video signal for the dementia patient, a determination unit for analyzing the signals, and determining features of the dementia patient, wherein the features include information about whether the dementia patient is in an unconscious state during generation of the physiological signals and whether the patient speaks words appropriate for a situation, and a symptom recognition unit for comparing features corresponding to respective dementia symptoms with features of the dementia patient, determining variations in cognitive ability, memory, and expressiveness based on a result of the comparison, and recognizing each dementia symptom.

18 Claims, 10 Drawing Sheets

(52) U.S. Cl.
CPC ............ *A61B 5/1124* (2013.01); *A61B 5/486* (2013.01); *A61B 5/6813* (2013.01); *A61B 5/746* (2013.01); *G16H 10/60* (2018.01)

(58) Field of Classification Search
CPC ..... A61B 5/1124; A61B 5/486; A61B 5/6813; A61B 5/746; G16H 10/60
See application file for complete search history.

(56) References Cited

U.S. PATENT DOCUMENTS

| | | | |
|---|---|---|---|
| 2007/0250119 A1* | 10/2007 | Tyler | A61N 1/36014 607/2 |
| 2009/0099783 A1* | 4/2009 | Reisberg | G06F 19/00 702/19 |
| 2009/0299645 A1* | 12/2009 | Colby | C12Q 1/6883 702/19 |
| 2010/0249638 A1* | 9/2010 | Liley | A61B 5/0476 600/544 |
| 2012/0150545 A1* | 6/2012 | Simon | A61B 5/0476 704/270 |
| 2012/0157790 A1* | 6/2012 | Park | A61B 5/0002 600/300 |
| 2013/0176127 A1* | 7/2013 | Junqua | G06F 17/30292 340/573.1 |
| 2014/0068255 A1 | 3/2014 | Park et al. | |
| 2014/0223462 A1* | 8/2014 | Aimone | H04N 21/42201 725/10 |
| 2014/0336479 A1* | 11/2014 | Ando | A61B 5/4041 600/310 |
| 2015/0223731 A1* | 8/2015 | Sahin | A61B 5/16 600/301 |
| 2017/0258329 A1* | 9/2017 | Marsh | A61B 5/0024 |
| 2017/0258390 A1* | 9/2017 | Howard | A61B 5/16 |
| 2017/0365101 A1* | 12/2017 | Samec | G02B 27/017 |
| 2018/0082037 A1* | 3/2018 | Arbouzov | G06F 19/3418 |
| 2018/0214122 A1* | 8/2018 | Ansell | A61B 5/7267 |
| 2018/0333306 A1* | 11/2018 | Ahong | A61B 5/6843 |

\* cited by examiner

APPARATUS AND METHOD FOR RECOGNIZING SYMPTOMS OF DEMENTIA AND PROVIDING DEMENTIA PATIENT MANAGEMENT SERVICE

CROSS REFERENCE TO RELATED APPLICATION

This application claims the benefit of Korean Patent Application No. 10-2015-0139696, filed Oct. 5, 2015, which is hereby incorporated by reference in its entirety into this application.

BACKGROUND OF THE INVENTION

1. Technical Field

The present invention relates generally to technology for recognizing the symptoms of dementia and providing a dementia patient management service and, more particularly, to technology for predicting dementia or recognizing the dementia progression of each dementia patient in real time and managing the private and daily life of the dementia patient.

2. Description of the Related Art

With the advent of an aging society, the number of dementia patients has increased. As a result, the seriousness of the social response to the increase in the number of dementia patients has become an issue. In particular, in homes or patient management institutions, protection management systems designed especially for dementia patients and configured to recognize the signs of dementia and protect and manage dementia patients have not yet been presented.

Therefore, there is urgently required the development of technology that can be utilized in homes or dementia patient management institutions, that is designed especially for dementia patients, and that is configured to recognize the signs of dementia and recognize the progression of dementia symptoms.

Korean Patent Application Publication No. 2010-0026302 discloses a system for managing an elderly or infirm person using a mobile terminal. In particular, this system discloses technology for monitoring information about an elderly or infirm person, which includes information about the location of the elderly or infirm person, transmitting the information about the elderly or infirm person to the terminal of a specialist, receiving instructions from the specialist, and transmitting the instructions to the terminal of the elderly or infirm person.

However, the technology disclosed in Korean Patent Application Publication No. 2010-0026302 is fatally problematic in that the management of dementia patients is still dependent on a specialist, and it is impossible to automatically recognize the dementia symptoms of dementia patients.

Therefore, in consideration of various problems appearing due to the rapid advent of an aging society, that is, an increase in the number of dementia patients and an increase in social expenses for dementia patients, technology for more efficiently managing dementia patients is urgently required.

SUMMARY OF THE INVENTION

Accordingly, the present invention has been made keeping in mind the above problems occurring in the prior art, and an object of the present invention is to automatically recognize dementia using a sensor for sensing the signs of dementia.

Another object of the present invention is to provide a dementia patient management service and to automatically send a message to an acquaintance of a dementia patient.

In accordance with an aspect of the present invention to accomplish the above objects, there is provided an apparatus for recognizing dementia symptoms, including a reception unit for receiving physiological signals of a dementia patient collected by sensors corresponding to a dementia detection device, an ambient environmental information signal, a location signal, a motion signal, an audio signal, and a video signal corresponding to the dementia patient; a determination unit for analyzing the signals, and determining features of the dementia patient, wherein the features include information about whether the dementia patient is in an unconscious state during generation of the physiological signals and whether the patient correctly speaks words appropriate for a situation; and a symptom recognition unit for comparing features corresponding to respective dementia symptoms with features of the dementia patient, determining variations in cognitive ability, memory, and expressiveness based on a result of the comparison, and recognizing each dementia symptom based on the variations.

The symptom recognition unit may set a level of each dementia symptom based on a result of recognizing the dementia symptom.

The symptom recognition unit may analyze an association between the environmental information signal and the dementia symptom and determines a frequency of occurrence of the dementia symptom and a rate of variation in the dementia symptom depending on the ambient environment based on the association.

The symptom recognition unit may determine rates of variation in the dementia symptom for respective time spans, rates of variation in the dementia symptom for respective temperatures, and rates of variation in the dementia symptom for respective humidity values.

The determination unit may be configured to determine whether a physiological phenomenon has occurred based on the physiological signals, and is configured to, when the physiological phenomenon has occurred, determine that the dementia patient has a physiological phenomenon in an unconscious state if a management service request signal is not received or if a temperature physiological signal value and a humidity physiological signal value, which are measured after lapse of a preset period of time, fall within a specific range.

The determination unit may be configured to determine based on the location signal whether the patient has deviated from a designated location, and to check based on the location signal whether the patient has safely returned to the designated location when the patient has deviated from the designated location, and the symptom recognition unit may be configured to recognize the dementia symptom based on a rate of increase in a number of unconscious deviations from the designated location when the rate of increase is equal to or greater than a specific value.

The symptom recognition unit may receive family history information of the dementia patient, daily life information of the dementia patient, and medical examination information of the dementia patient, and recognize the dementia symptom based on the received information and the variations in cognitive ability, memory, and expressiveness.

In accordance with another aspect of the present invention to accomplish the above objects, there is provided an apparatus for providing a dementia patient management service, including an analysis unit for receiving physiological signals of a dementia patient collected by sensors corresponding to a dementia detection device, an ambient environmental information signal, a location signal, a motion signal, an audio signal, and a video signal corresponding to the dementia patient, analyzing the signals, and analyzing a current condition of the dementia patient; and a service provision unit for providing a warning service corresponding to a specific situation and a notification service to an acquaintance of the dementia patient if it is determined, based on a result of a comparison between a preset condition of the dementia patient and the current condition of the dementia patient, that the current condition of the dementia patient indicates the specific situation.

The service provision unit may determine whether to provide the notification service based on a level of the dementia symptom.

The service provision unit may be configured to provide both the warning service and the notification service when the level of the dementia symptom is any one of a high level and a middle level, and provide only a warning service when the level of the dementia symptom is a low level.

The service provision unit may be configured to determine the location of the dementia patient based on the location signal, and to provide the notification service to an acquaintance located closest to the dementia patient among registered acquaintances.

The service provision unit may deliver a notification service including one or more of a physiological phenomenon and location information using a Short Message Service (SMS).

In accordance with a further aspect of the present invention to accomplish the above objects, there is provided a method for recognizing dementia and providing a dementia patient management service, including receiving physiological signals of a dementia patient collected by sensors corresponding to a dementia detection device, an ambient environmental information signal, a location signal, a motion signal, an audio signal, and a video signal corresponding to the dementia patient, analyzing the signals, and determining features of the dementia patient, wherein the features include information about whether the dementia patient is in an unconscious state during generation of the physiological signals and whether the patient correctly speaks words appropriate for a situation; analyzing features corresponding to respective dementia symptoms and the features of the dementia patient, determining variations in cognitive ability, memory, and expressiveness based on a result of analysis, and recognizing each dementia symptom based on the variations; and providing a warning service corresponding to a specific situation and a notification service to an acquaintance of the dementia patient if it is determined, based on a result of a comparison between a preset condition of the dementia patient and a current condition of the dementia patient, that the current condition of the dementia patient indicates a specific situation.

Recognizing each dementia symptom may be configured to set a level of each dementia symptom based on a result of recognizing the dementia symptom.

Providing the notification service may be configured to determine whether to provide the notification service based on the level of the dementia symptom.

Providing the notification service may include provide both the warning service and the notification service when the level of the dementia symptom is any one of a high level and a middle level, and provide only the warning service when the level of the dementia symptom is a low level.

Providing the notification service may be configured to deliver a notification service including one or more of a physiological phenomenon and location information using a Short Message Service (SMS).

Recognizing each dementia symptom may be configured to analyze an association between the environmental information signal and the dementia symptom and determine a frequency of occurrence of the dementia symptom and a rate of variation in the dementia symptom depending on the ambient environment based on the association.

Recognizing each dementia symptom may be configured to determine whether a physiological phenomenon has occurred based on the physiological signals, and is configured to, when the physiological phenomenon has occurred, determine that the dementia patient has a physiological phenomenon in an unconscious state if a management service request signal is not received or if a temperature physiological signal value and a humidity physiological signal value, which are measured after lapse of a preset period of time, fall within a specific range.

Recognizing each dementia symptom may be configured to receive family history information, daily life information, and medical examination information of the dementia patient, and recognize the dementia symptom based on the received information and the variations in cognitive ability, memory, and expressiveness.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
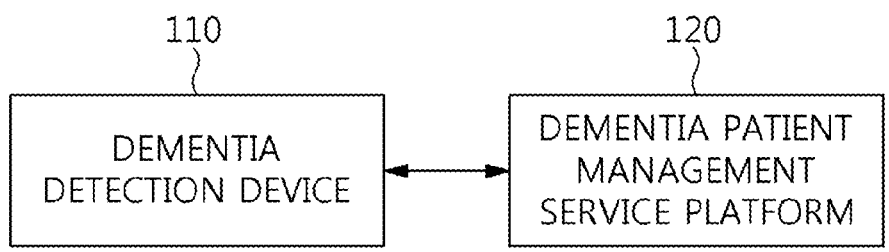
FIG. 1 is a block diagram showing a dementia patient management service platform and a dementia detection device according to an embodiment of the present invention.

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Hereinafter, preferred embodiments of the present invention will be described in detail with reference to the attached drawings.

FIG. 1 is a block diagram showing a dementia patient management service platform and a dementia detection device according to an embodiment of the present invention.

Referring to FIG. 1, a system for managing dementia patients according to an embodiment of the present invention includes a dementia detection device 110 and a dementia patient management service platform 120.

The dementia detection device 110 may sense a signal corresponding to the condition of a dementia patient using sensors, and may transfer the sensed signals to the dementia patient management service platform 120.

Here, the dementia detection device 110 may include a dementia detection signal sensing unit, a sensed signal processing unit, and a sensed signal transmission unit.

The dementia detection sensing unit may sense a signal including one or more of physiological signals, an audio signal, a video signal, an image signal, an environment signal (including temperature, humidity and time), a physical activity and motion strength signal, and a location signal, which are related to a dementia subject (dementia patient)'s body.

Here, sensors for sensing the physiological signals, the audio signal, the motion signal, and the location signal may be applied to a wearable device.

Further, sensors for sensing the audio signal, the environment signal, the motion signal, and the location signal may be applied to a personal mobile smart phone.

Furthermore, sensors for sensing the audio signal and the environmental signal may be applied to a Personal Computer (PC) or a server to which the dementia patient management service platform 120 is applied.

Furthermore, sensors for sensing the video signal may be applied to a Closed Circuit Television (CCTV).

Here, in order to configure the dementia detection signal sensing unit, sensors for sensing physiological signals, a motion signal, an audio signal, and a location signal must be included therein, or, alternatively, sensors for sensing a video signal or an environment signal may be used therefor.

Here, the signal corresponding to the condition of the dementia patient may be a signal having various types of information, and is not limited to specific information belonging to the signal. For example, a defecation signal, a temperature signal, a humidity signal, or the like may be the signal corresponding to the condition of the dementia patient.

The dementia patient management service platform 120 may recognize the signs and symptoms of dementia based on the signals received from the dementia detection device 110, and may perform a function of preventing and treating dementia and taking measures against a specific situation using the recognized signs and symptoms.

The dementia patient management service platform is composed of a dementia symptom recognition apparatus and a dementia patient management service provision apparatus, and a description thereof will be made in detail below with reference to FIG. 2.

Figure 2:
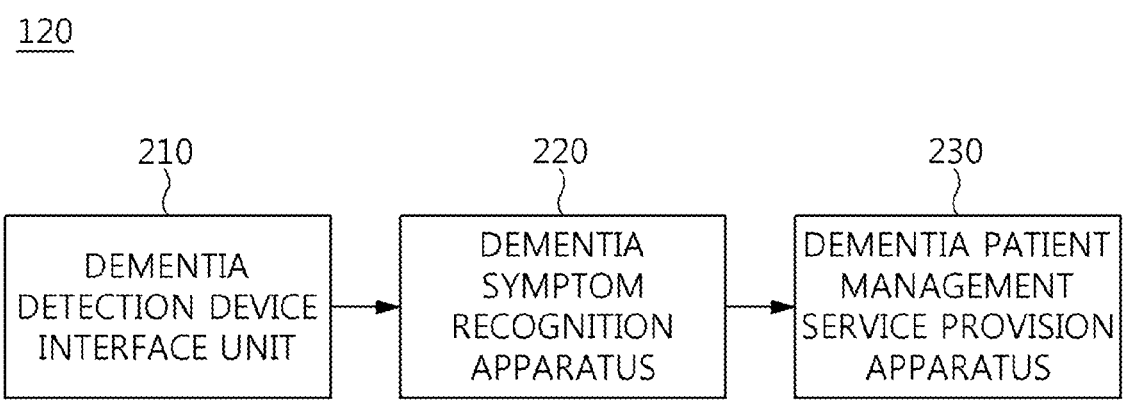
FIG. 2 is a block diagram showing the dementia patient management service platform shown in FIG. 1.

FIG. 2 is a block diagram showing the dementia patient management service platform shown in FIG. 1.

Referring to FIG. 2, the dementia patient management service platform 120 includes a dementia detection device interface unit 210, a dementia symptom recognition apparatus 220, and a dementia patient management service provision apparatus 230.

The dementia detection device interface unit 210 may set up a connection between the dementia detection device and the dementia patient management service platform, process a communication protocol, and receive multiple messages based on multi-modal, multi-channel communication.

Here, since the signal transmitted from the dementia detection device 110 includes multiple signals, the dementia detection device interface unit 210 may parse, store and manage multiple sensed signals.

The dementia symptom recognition apparatus 220 and the dementia patient management service provision apparatus 230 will be described in detail later below with reference to FIGS. 3 and 4.

Figure 3:
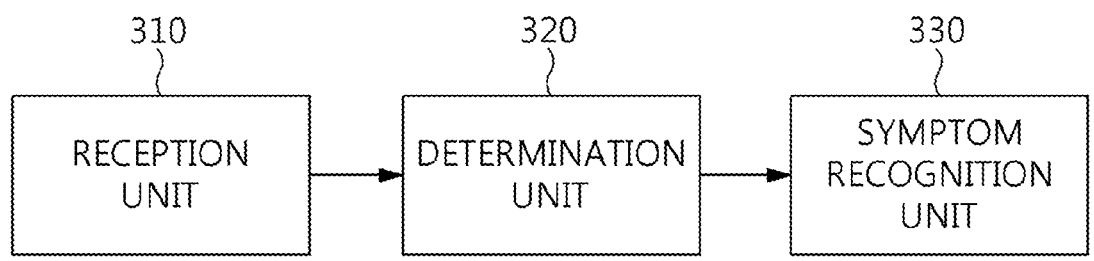
FIG. 3 is a block diagram showing the dementia symptom recognition apparatus shown in FIG. 2.

FIG. 3 is a block diagram showing the dementia symptom recognition apparatus shown in FIG. 2.

Referring to FIG. 3, the dementia symptom recognition apparatus according to an embodiment of the present invention includes a reception unit 310, a determination unit 320, and a symptom recognition unit 330.

The reception unit 310 receives signals collected by sensors corresponding to the dementia detection device, that is, physiological signals, an ambient environmental information signal, a location signal, a motion signal, an audio signal, and a video signal for a dementia patient.

Here, such a physiological signal may mean a signal generated when the dementia patient urinates or has a bowel movement.

Here, the ambient environmental information signal may be a signal including one or more of the ambient temperature and humidity in the vicinity of the dementia patient and the time.

The audio signal may mean a signal obtained by recording the voice of the dementia patient.

The video signal may mean a signal obtained by imaging the dementia patient so as to monitor the symptoms of the dementia patient and analyze the condition of the dementia patient.

The motion signal may mean a signal including the motion radius, walking speed and walking direction of the dementia patient.

In this case, the reception unit 310 may perform signal synchronization for analyzing symptoms for multiple received signals in the same time span.

The determination unit 320 analyzes the signals and determines the features of the dementia patient, including information about whether the dementia patient is in an unconscious state during the generation of the physiological signal and whether the dementia patient correctly speaks words or phrases appropriate for the situation.

Here, the determination unit 320 may analyze the characteristics of signals required to recognize the symptoms and signs of the dementia patient, and may extract and analyze pieces of information that influence the occurrence of dementia.

In this case, whether the dementia patient is in an unconscious state may indicate whether a physiological phenomenon is due to the conscious behavior of the dementia patient when the physiological phenomenon occurs. For example, typical dementia patients may have a physiological phenomenon such as unintentional urination or defecation. That is, the determination unit 320 may detect such an unintentional physiological phenomenon.

When a management service request attributable to the occurrence of a physiological phenomenon is not received, or when a previously sensed temperature/humidity physiological signal value is maintained even after the lapse of a predetermined period of time, the determination unit 320 may determine that the patient is in an unconscious (insensible) state, and may determine that a physiological phenomenon has occurred in an unconscious state when the occurrence of the physiological phenomenon is sensed in response to a physiological signal.

The symptom recognition unit 330 may compare features corresponding to respective symptoms of dementia with the features of the dementia patient, determine variations in cognitive ability, memory, and expressiveness based on the results of the comparison, and recognize the symptoms of dementia.

The symptom recognition unit 330 may analyze the influence of environmental information on the manifestation of the symptoms of dementia. That is, the symptom recognition unit 330 may analyze the association between the environmental information signals and the symptoms of dementia, and may determine the frequency of occurrence of dementia symptoms and the rate of variation in dementia symptoms depending on the ambient environment based on the association. For example, it may be determined that when the temperature is high, the frequency of occurrence of dementia symptoms is high, or when the humidity is high, the frequency of occurrence of dementia symptoms is high.

Here, the symptom recognition unit 330 may determine the rates of variation in dementia symptoms for respective time spans, the rates of variation in dementia symptoms for respective temperatures, and the rates of variation in dementia symptoms for respective humidity values. Based on the results of the determination by the symptom recognition unit 330, an environment in which the symptoms of the dementia patient may be minimized may be created.

Here, the symptom recognition unit 330 may set the level of dementia symptoms based on the results of recognition of dementia symptoms. For example, the features corresponding to respective dementia symptoms are compared with the features of the dementia patient. When the number of times that the same symptom appears is greater than a specific number, the level of dementia may be set to a high level, whereas when the number of times that the same symptom appears is less than or equal to the specific number, the level of dementia may be set to a middle or low level.

Here, the symptom recognition unit 330 may extract features for respective dementia symptoms, extract integrated features required to recognize the symptoms of dementia, and produce dementia symptoms through a procedure for integrally analyzing associations therebetween.

In this case, the symptom recognition unit 330 may receive family history information of the dementia patient, daily life information of the dementia patient, and medical examination information of the dementia patient, and may recognize dementia symptoms based on the received information, variation in cognitive ability, variation in memory, and variation in expressiveness.

Here, the family history information of the dementia patient is configured to store and manage data input depending on the items required to analyze the influence of dementia, such as family members in a direct line or the name of the corresponding disease.

The medical examination information from medical institutions is configured to store and manage data input for inputting items that are required in order to analyze dementia symptoms and the progression of the symptoms, such as the results of periodically taken Magnetic Resonance Imaging (MRI) pictures, the results of ultrasonic scans, and blood test results acquired from the medical institutions, and information and opinions, such as the records of determination made by specialists.

The information required to determine the degree of the decline in cognitive ability may mean information about the degree to which the patient recognizes his or her family, acquaintances, objects or locations.

In this case, information required to determine the degree of the decline in memory may mean information about whether the patient correctly guesses the content of a picture or an image shown to the patient after the lapse of a predetermined period of time, or whether the patient correctly finds a word shown to the patient after the lapse of a predetermined period of time. Further, memory information may be collected in such a way that a word is played to the patient through a speaker, and the patient correctly guesses the played word.

Here, information required to determine the degree of the decline in expressiveness is configured to receive and store information such as the details and the number of expressions inappropriate for a situation (context) and the reason, such as information about unexpected words and actions, in order to collect information about a command of a language inappropriate for a situation and the associated reason.

Here, the dementia symptom recognition apparatus may further include a dementia patient information management unit (not shown) for managing information about the dementia patient.

The dementia patient information management unit may manage information generated via self-diagnosis, manage the degree of the mental state of the dementia patient, manage information about accumulated recognized dementia symptoms, or manage information about the area of activity of the dementia patient. Further, information about a dementia subject (or dementia patient) and information corresponding to contextual information may be accumulated and managed.

Figure 4:
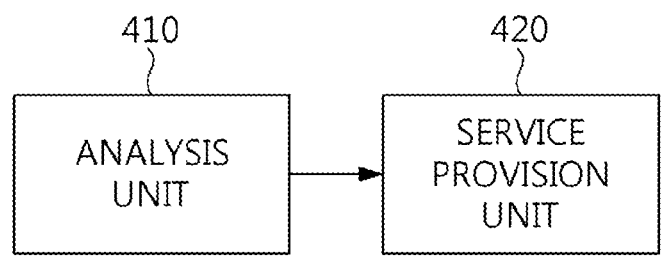
FIG. 4 is a block diagram showing the dementia patient management service provision apparatus shown in FIG. 2.

FIG. 4 is a block diagram showing the dementia patient management service provision apparatus shown in FIG. 2.

Referring to FIG. 4, the dementia patient management service provision apparatus includes an analysis unit 410 and a service provision unit 420.

The analysis unit 410 receives a physiological signal, an ambient environmental information signal, a location signal, a motion signal, an audio signal, and a video signal for a dementia patient, which are collected by sensors corresponding to the dementia detection device, analyzes the received signals, and then analyzes the current condition of the dementia patient.

When it is determined, based on the results of comparing the preset condition of the dementia patient with the current condition of the dementia patient, that the current condition of the dementia patient indicates a specific situation, the service provision unit 420 may provide a warning service corresponding to the specific situation and a notification service to the acquaintance of the dementia patient.

Here, the warning service may denote a service that displays a situation faced by the dementia patient on the device of the dementia patient. In an example, when the patient has a physiological phenomenon that reflects an unconscious state, a warning service indicating that the physiological phenomenon has occurred may be provided. Further, in another example, when the dementia patient deviates from a designated location, a warning service indicating the deviation of the dementia patient from the designated location may be provided.

In this case, the service provision unit 420 determines whether to provide a notification service based on the level of dementia symptoms. When the level of dementia symptoms corresponds to one of a high level and a middle level, both a warning service and a notification service may be provided. When the level of dementia symptoms corresponds to a low level, which is relatively low, only a warning service may be provided.

When the level of dementia corresponds to a middle or high level, when the patient has a mobility disability, when a physiological phenomenon occurs, or when the patient deviates from the designated location, a notification service may be provided to the acquaintance or caretaker of the patient.

Here, the notification service may include information about the time and location at which the corresponding notification occurs.

The notification service may be delivered to the caretaker or the acquaintance of the patient using a Short Message Service (SMS), or may be delivered using a Social Network Service (SNS) corresponding to the caretaker or the acquaintance of the patient.

Here, the service provision unit 420 may provide self-diagnosis that allows the dementia patient himself or herself or the family of the patient to personally diagnose the condition of the patient. For example, the diagnosis of memory, the diagnosis of walking, the diagnosis of cognitive ability, the diagnosis of reaction speed, etc. may be provided.

Here, the service provision unit 420 may also provide a service for relieving or preventing dementia symptoms. For example, the rehabilitation of memory, vitality, cognitive ability, responsiveness, etc. may be provided.

The service provision unit 420 may provide a service to the caretaker of the patient. For example, a patient condition notification service for indicating the condition of a dementia patient when the dementia patient enters an emergency state, a service for monitoring the condition and location of the dementia patient, etc. may be provided. Further, a function of operating in conjunction with the device of the caretaker may also be provided.

The service provision unit 420 may also provide a test schedule notification service, an exercise time notification service, a bedtime notification service, a mealtime notification service, or the like.

Further, the service provision unit 420 may also provide a danger warning service, a location tracking service, an automatic relief request service, a movement/going-out detection service, or the like.

Figure 5:
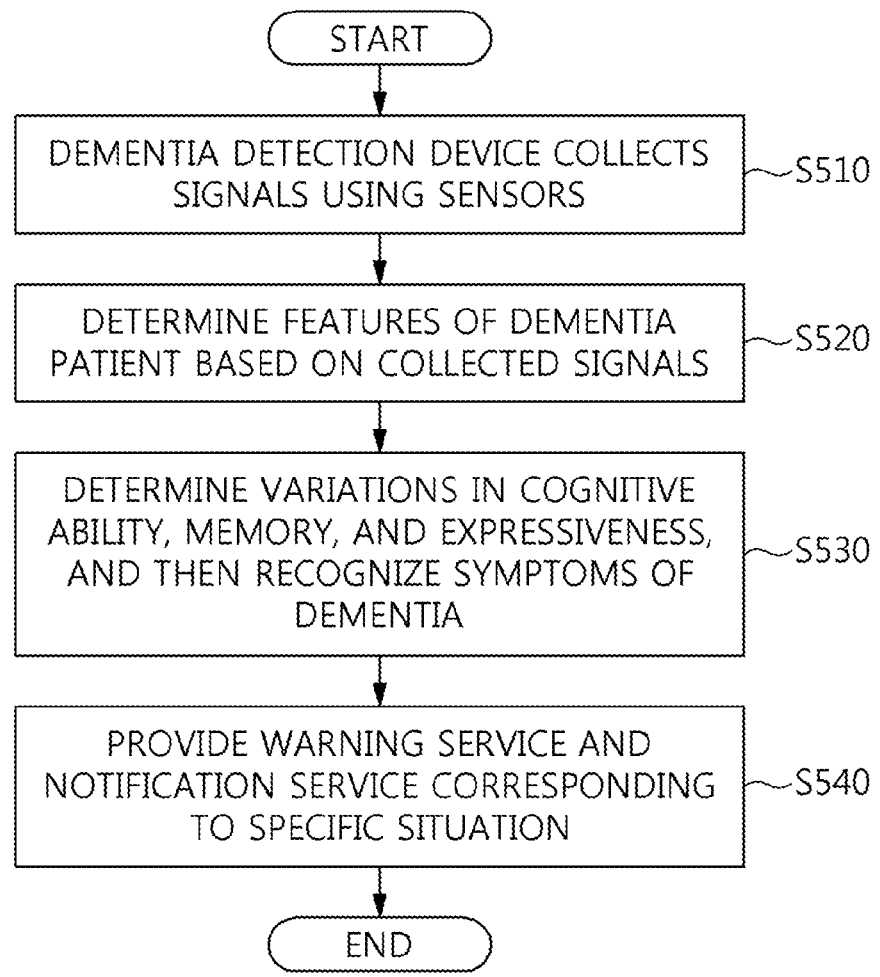
FIG. 5 is an operation flowchart showing a method for recognizing dementia and providing a dementia patient management service according to an embodiment of the present invention.

FIG. 5 is an operation flowchart showing a method for recognizing dementia and providing a dementia patient management service according to an embodiment of the present invention.

Referring to FIG. 5, the dementia detection device collects signals using sensors at step S510.

Here, the dementia detection device may collect a physiological signal, an ambient environmental information signal, an audio signal, a video signal, and a motion signal using sensors.

Here, the physiological signal may mean a signal generated when the dementia patient urinates or has a bowel movement.

The ambient environmental information signal may be a signal including one or more of the ambient temperature and humidity in the vicinity of the dementia patient and the time.

The audio signal may mean a signal obtained by recording the voice of the dementia patient.

The video signal may mean a signal obtained by imaging the dementia patient so as to monitor the symptoms of the dementia patient and analyze the condition of the dementia patient.

The motion signal may mean a signal including the motion radius, walking speed and walking direction of the dementia patient.

Next, the features of the dementia patient are determined based on the collected signals at step S520.

The determination unit 320 analyzes the signals and determines the features of the dementia patient, including information about whether the dementia patient is in an unconscious state during the generation of the physiological signal and whether the dementia patient correctly speaks words or phrases appropriate for the situation.

Here, the determination unit 320 may analyze the characteristics of signals required to recognize the symptoms and signs of the dementia patient, and may extract and analyze pieces of information that influence the occurrence of dementia.

In this case, whether the dementia patient is in an unconscious state may indicate whether a physiological phenomenon is due to the conscious behavior of the dementia patient when the physiological phenomenon occurs. For example, typical dementia patients may have a physiological phenomenon such as unintentional urination or defecation. That is, the determination unit 320 may detect such an unintentional physiological phenomenon.

Here, when the motion of the patient is found to be less than or equal to a specific value based on the location signal, the determination unit 320 may determine that the patient is in an unconscious state. When the occurrence of a physiological phenomenon is sensed in response to a physiological signal in the state in which the motion of the patient is less than or equal to the specific value, the determination unit 320 may determine that a physiological phenomenon has occurred while the dementia patient is in an unconscious state.

Further, when a management service request attributable to the occurrence of a physiological phenomenon is not received, or when a previously sensed temperature/humidity physiological signal value is maintained even after the lapse of a predetermined period of time, the determination unit 320 may determine that the patient has a physiological phenomenon in an unconscious (insensible) state. When the occurrence of a physiological phenomenon is sensed in response to a physiological signal, the determination unit 320 may determine that the physiological phenomenon has occurred in an unconscious state.

Furthermore, variations in cognitive ability, memory, and expressiveness may be determined, whereby the symptoms of dementia are recognized at step S530.

Here, the variations in cognitive ability, memory, and expressiveness are determined using the features of the dementia patient, which include information about whether the dementia patient is in an unconscious state while the physiological signal determined by the determination unit 320 is generated, and information about whether the dementia patient correctly speaks words or phrases appropriate for a situation.

Here, the determination unit 320 may determine the degree of the decline in expressiveness by checking the frequency of words inappropriate for the situation.

Further, a warning service and a notification service corresponding to a specific situation are provided at step S540.

Here, the warning service may denote a service that displays a situation faced by the dementia patient on the device of the dementia patient. In an example, when the patient has a physiological phenomenon that reflects an unconscious state, a warning service indicating that the physiological phenomenon has occurred may be provided. Further, in another example, when the dementia patient deviates from a designated location, a warning service indicating the deviation of the dementia patient from the designated location may be provided.

In this case, it is determined whether to provide a notification service based on the level of dementia symptoms. When the level of dementia symptoms corresponds to one of a high level and a middle level, both a warning service and a notification service may be provided. When the level of dementia symptoms corresponds to a low level, which is relatively low, only a warning service may be provided.

For example, when the level of dementia corresponds to a middle or high level, when the patient has a mobility disability, when a physiological phenomenon occurs, or when the patient deviates from the designated location, a notification service may be provided to the acquaintance or caretaker of the patient.

Here, the notification service may include information about the time and location at which the corresponding notification occurs.

The notification service may be delivered to the caretaker or the acquaintance of the patient using a Short Message Service (SMS), or may be delivered using a Social Network Service (SNS) corresponding to the caretaker or the acquaintance of the patient.

Here, it is possible to provide self-diagnosis that allows the dementia patient himself or herself or the family of the patient to personally diagnose the condition of the patient. For example, the diagnosis of memory, the diagnosis of walking, the diagnosis of cognitive ability, the diagnosis of reaction speed, etc. may be provided.

It is also possible to provide a service for relieving or preventing dementia symptoms. For example, the rehabilitation of memory, vitality, cognitive ability, responsiveness, etc. may be provided.

Further, a service may be provided to the caretaker of the patient. For example, a patient condition notification service for indicating the condition of a dementia patient when the dementia patient enters an emergency state, a service for monitoring the condition and location of the dementia patient, etc. may be provided. Further, a function of operating in conjunction with the device of the caretaker may also be provided.

It is also possible to provide a test schedule notification service, an exercise time notification service, a bedtime notification service, a mealtime notification service, or the like.

Further, it is also possible to provide a danger warning service, a location tracking service, an automatic relief request service, a movement/going-out detection service, or the like.

Figure 6:
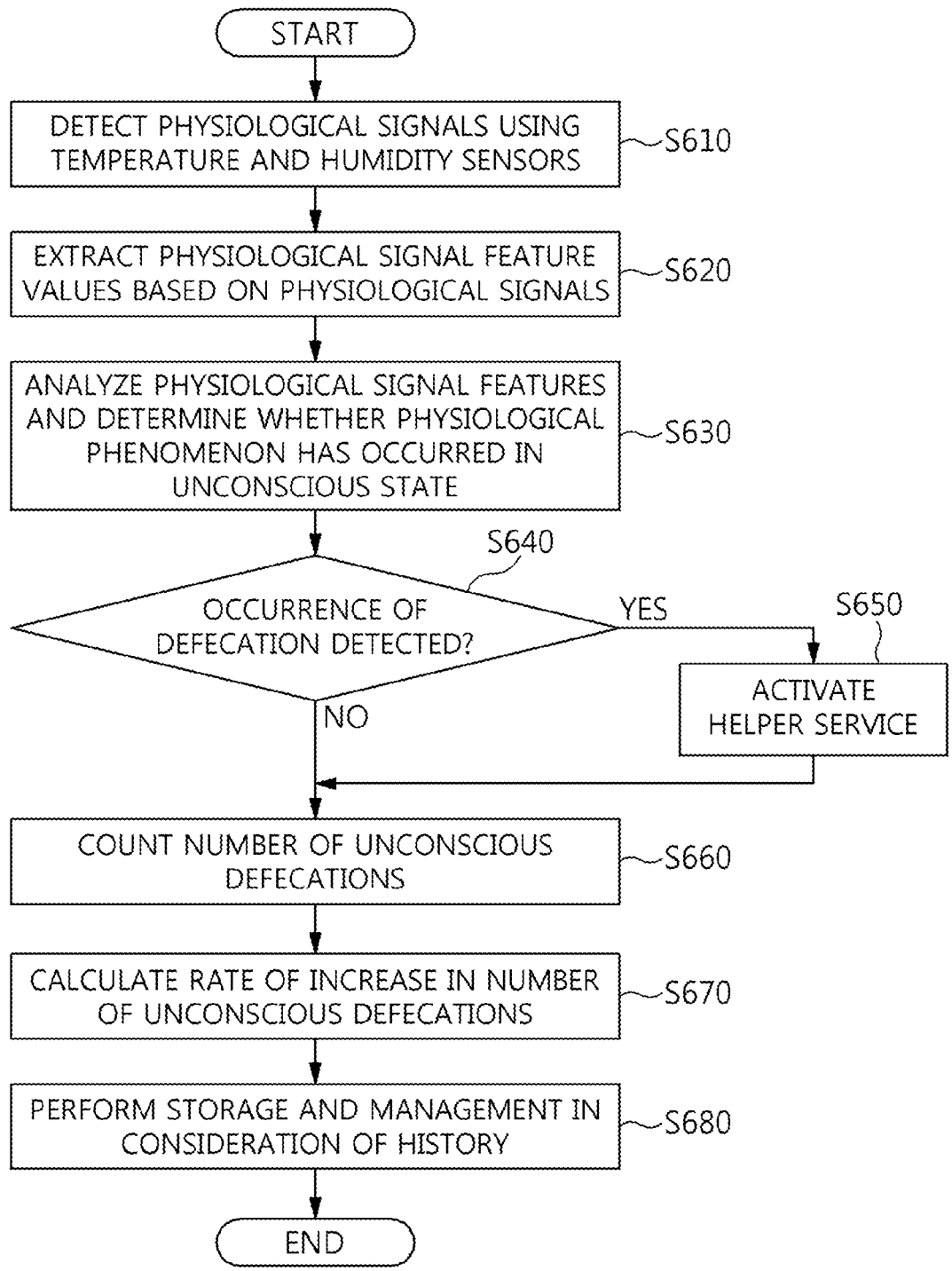
FIG. 6 is an operation flowchart showing a procedure for detecting dementia and providing a dementia patient management service based on physiological signals in the method for recognizing dementia and providing the dementia patient management service according to an embodiment of the present invention.

FIG. 6 is an operation flowchart showing a procedure for detecting dementia and providing a dementia patient management service based on physiological signals in the method for recognizing dementia and providing the dementia patient management service according to an embodiment of the present invention.

Referring to FIG. 6, physiological signals are detected using a temperature sensor and a humidity sensor installed on a wearable device (e.g. a diaper, underpants, etc.) at step S610.

For example, when a dementia patient urinates, temperature and humidity are rapidly increased. The reason for this is that urine is liquid, the temperature of which is higher than the body temperature. Further, when the dementia patient urinates without taking appropriate measures, the high temperature and high humidity are uniformly maintained. Therefore, the physiological signals may be generated based on the temperature value and the humidity value detected by the temperature sensor and the humidity sensor.

Further, the feature values of the physiological signals are extracted based on the physiological signals at step S620, the features of the physiological signals are analyzed using the feature values, and it is determined whether a physiological phenomenon occurs in an unconscious state at step S630.

Here, when the dementia patient urinates without taking appropriate measures, the high temperature and high humidity are uniformly maintained. Thus, when the high temperature and high humidity are maintained for a specific period of time or longer (e.g. there is no limitation requiring that the time length be set to one or more minutes, but the time length may of course be set to two or more minutes), a physiological signal feature value (set to '1' in the case of urine, and '11' in the case of feces, without, of course, this setting method being limited thereto) may be extracted, and the features of the corresponding physiological signal may be analyzed.

Here, methods for determining whether a physiological phenomenon has occurred in an unconscious state include a method for determining whether the patient is unconscious using temperature/humidity signal information sensed via the processing of underpants performed in response to a management service request attributable to the occurrence of a physiological phenomenon. For example, when a management service request attributable to the occurrence of the physiological phenomenon of the patient is received or when the sensed temperature/humidity physiological signal value is reduced within a predetermined period of time, there is a high probability that the patient is in a conscious state. In contrast, when a management service request attributable to the occurrence of a physiological phenomenon is not received or when the sensed temperature/humidity physiological signal value is maintained even after the lapse of a predetermined period of time, there is a high probability that the patient is in an unconscious state. Accordingly, whether a physiological phenomenon has occurred in an unconscious state may be determined using a management service request attributable to the occurrence of a physiological phenomenon and wearable (temperature/humidity) underpants sensors.

Further, whether defecation occurs is determined at step S640. If it is determined that defecation occurs, a helper service is activated at step S650.

Here, whether defecation occurs may be determined using the results of analyzing the features of the physiological signals.

A description of the helper service will be made in detail later with reference to FIGS. 11 and 12.

Further, the number of unconscious defecations is counted at step S660, and the rate of increase in the number of unconscious defecations is calculated at step S670.

In this case, the rate of increase in the number of unconscious defecations may be used by the dementia detection device to determine the level of dementia.

Figure 10:
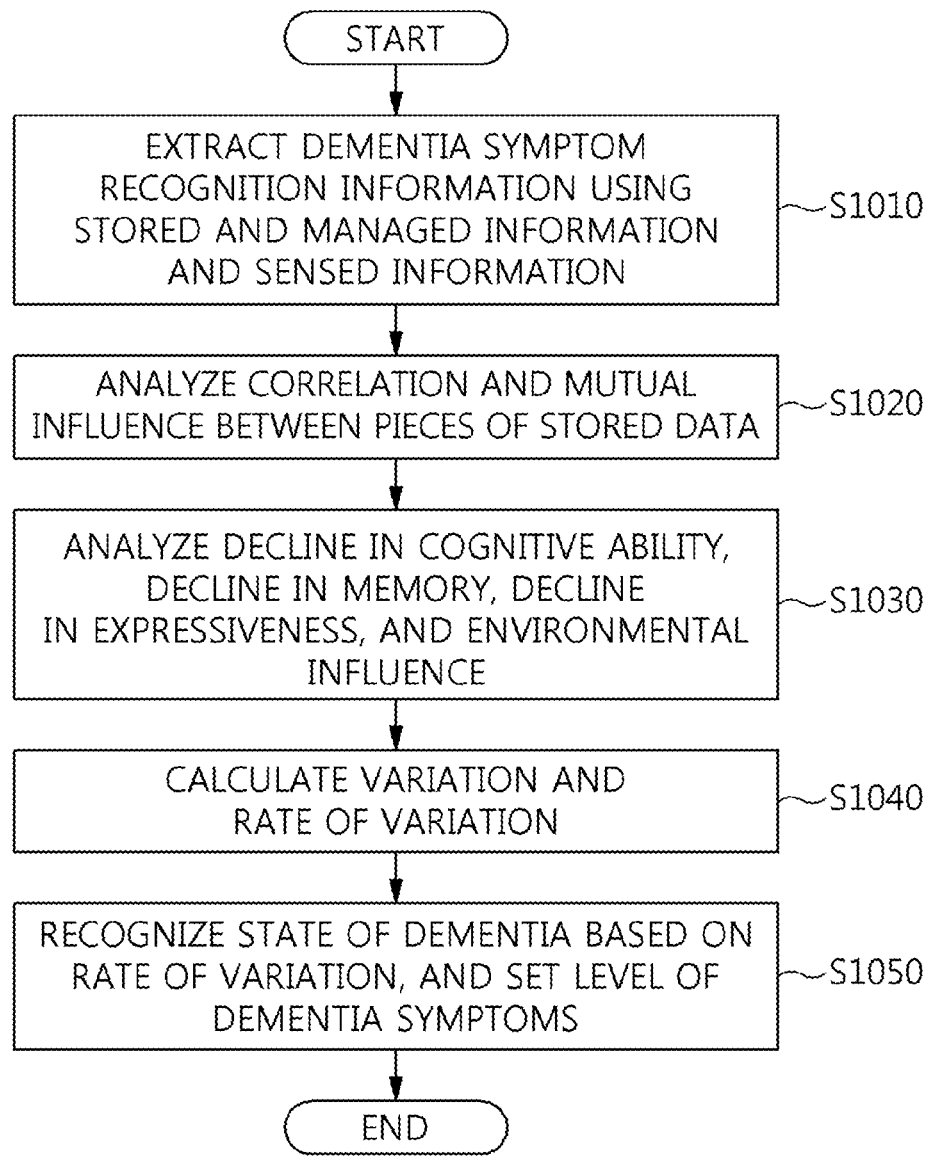
FIG. 10 is an operation flowchart showing a procedure for recognizing the symptoms of dementia in the method for recognizing dementia and providing the dementia patient management service according to an embodiment of the present invention.

It is apparent that the number of unconscious defecations and the rate of increase in the number of unconscious defecations may be stored and managed for use by the dementia symptom recognition engine in predicting and recognizing dementia, shown in FIG. 10.

Figure 7:
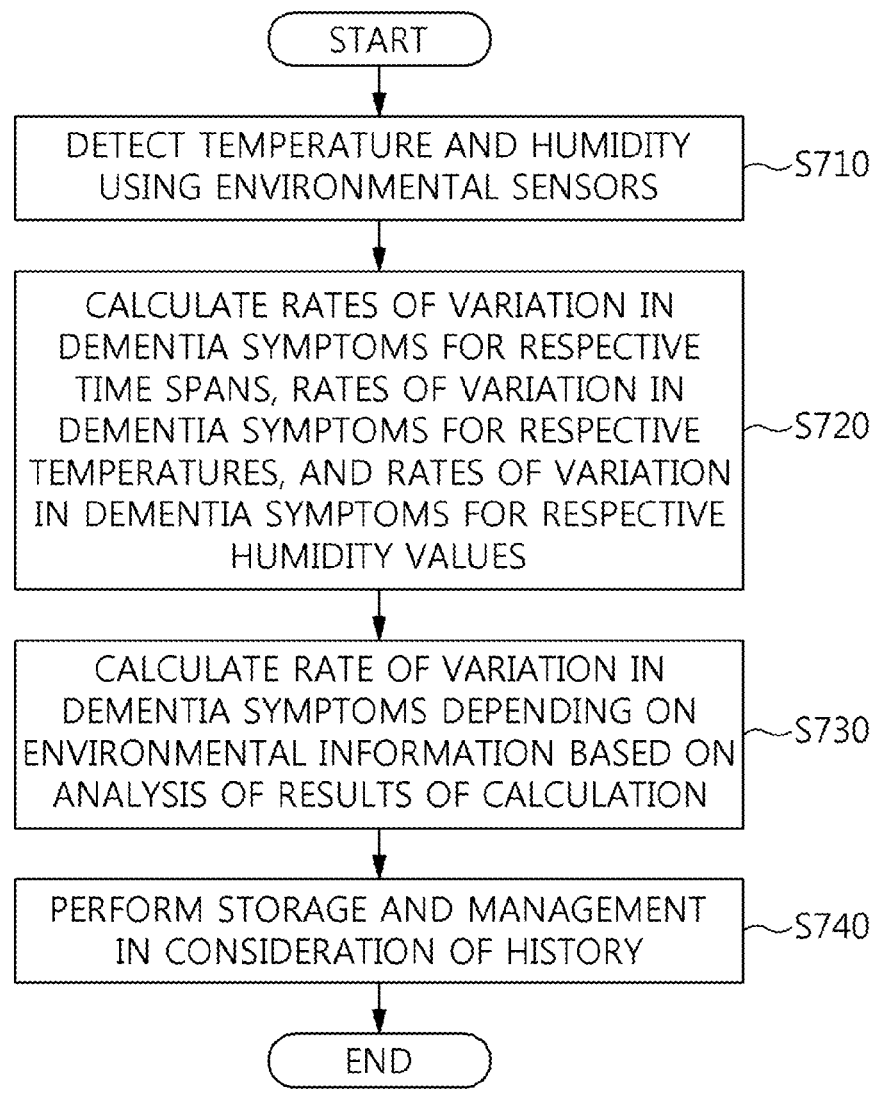
FIG. 7 is an operation flowchart showing a procedure for calculating the rate of variation in dementia symptoms using an environmental sensor in the method for recognizing dementia and providing the dementia patient management service according to an embodiment of the present invention.

FIG. 7 is an operation flowchart showing a procedure for calculating the rate of variation in dementia symptoms using an environmental sensor in the method for recognizing dementia and providing the dementia patient management service according to an embodiment of the present invention.

Referring to FIG. 7, temperature and humidity are detected using environmental sensors at step S710.

Further, the rates of variation in dementia symptoms for respective time spans, the rates of variation in dementia symptoms for respective temperatures, and the rates of variation in dementia symptoms for respective humidity values are calculated at step S720.

Based on the results of the calculation, the rate of variation in dementia symptoms depending on the environmental information is calculated based on the analysis of results of the calculation at step S730.

In this case, the rate of variation in dementia symptoms depending on the environmental information may be stored and managed for use by the dementia symptom recognition engine in predicting and recognizing dementia, shown in FIG. 10 at step S740. Environmental information in which the occurrence of dementia symptoms is minimized may be used to relieve dementia symptoms by applying the environmental information to the space in which the corresponding dementia patient is present.

Figure 8:
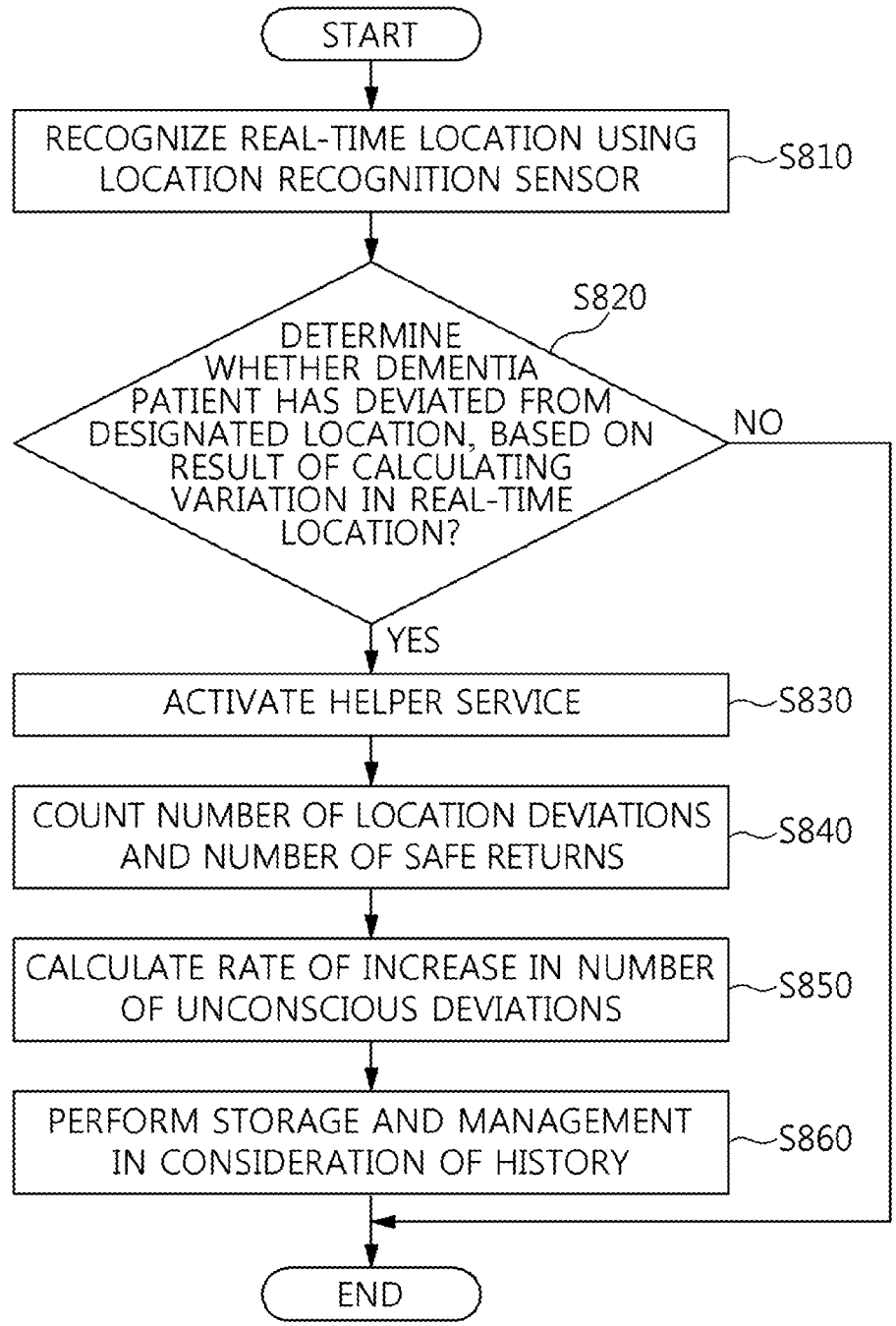
FIG. 8 is an operation flowchart showing a procedure for detecting dementia and providing a dementia patient management service based on real-time location signals in the method for recognizing dementia and providing the dementia patient management service according to an embodiment of the present invention.

FIG. 8 is an operation flowchart showing a procedure for detecting dementia and providing a dementia patient management service based on real-time location signals in the method for recognizing dementia and providing the dementia patient management service according to an embodiment of the present invention.

Referring to FIG. 8, the real-time location of a dementia patient is recognized using a location recognition sensor at step S810.

Further, whether the dementia patient has deviated from his or her designated location is determined based on the result of calculating variation in the real-time location at step S820.

Here, when the result of calculating the variation in real-time location is greater than a preset value, it may be determined that the dementia patient has deviated from the designated location. For example, when the result of calculating the variation in real-time location is greater than the preset value corresponding to the radius of a house in which the dementia patient is present, it may be determined that the dementia patient has deviated from the designated location.

Here, if the dementia patient has deviated from the designated location, a helper service is activated at step S830, and the number of deviations from the designated location and the number of safe returns are counted at step S840.

A description of the helper service will be made in detail with reference to FIGS. 11 and 12.

Further, the rate of increase in the number of unconscious deviations is calculated at step S850.

In this case, the rate of increase in the number of unconscious deviations may be used to determine the dementia level of the dementia patient. The rate of increase in the number of unconscious deviations, the number of deviations from the designated location, and the number of safe returns may be stored for use by the dementia symptom recognition engine in predicting and recognizing dementia, as shown in FIG. 10, at step S860.

Figure 9:
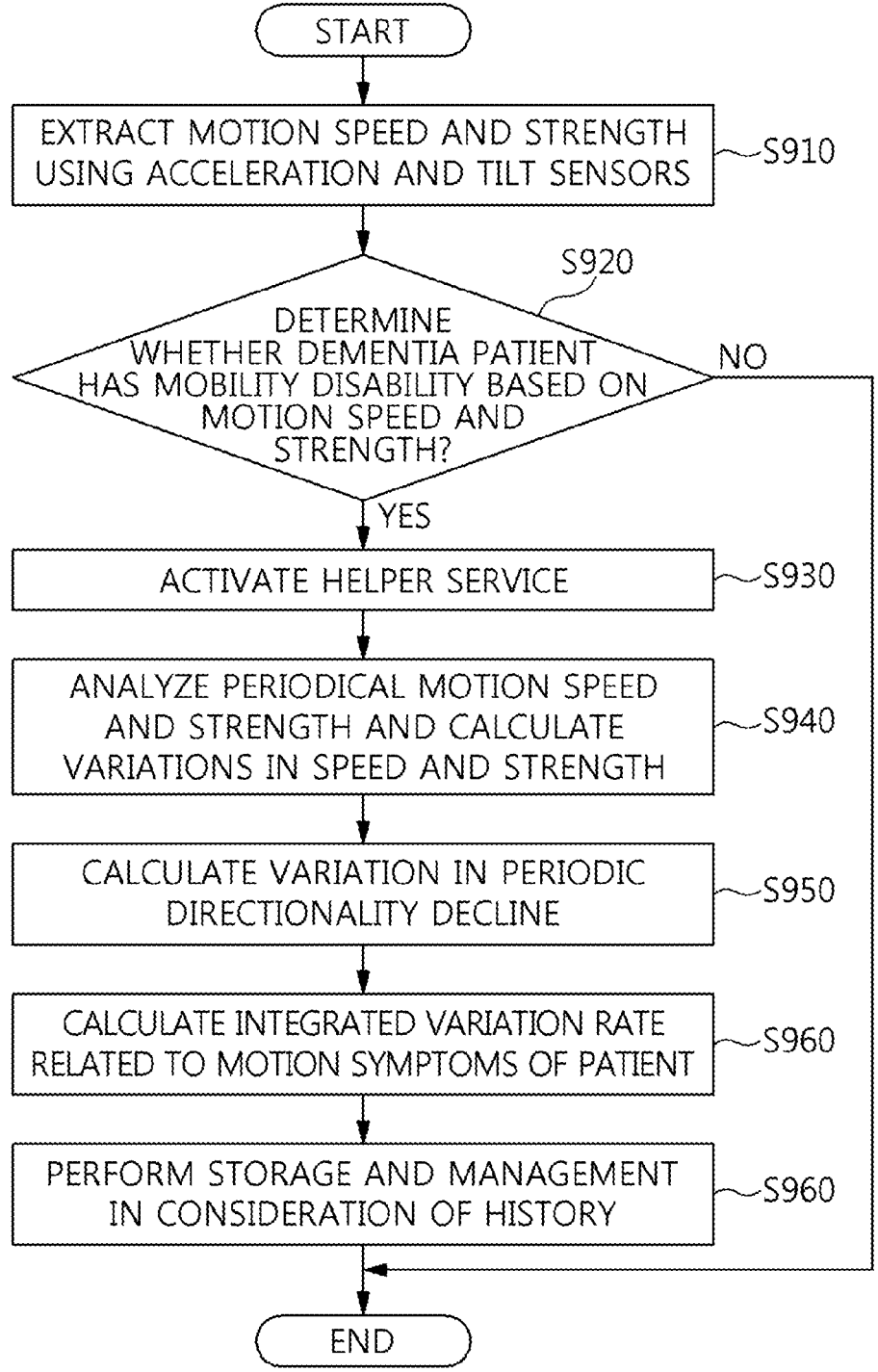
FIG. 9 is an operation flowchart showing a procedure for detecting dementia and providing a dementia patient management service based on motion speed and strength signals in the method for recognizing dementia and providing the dementia patient management service according to an embodiment of the present invention.

FIG. 9 is an operation flowchart showing a procedure for detecting dementia and providing a dementia patient management service based on motion speed and strength signals in the method for recognizing dementia and providing the dementia patient management service according to an embodiment of the present invention.

Referring to FIG. 9, the speed and strength of motion are detected using an acceleration sensor and a tilt sensor at step S910.

Here, whether the direction of a dementia patient who is directed to a target point is maintained may be detected, and information about the direction of motion, which is required to observe whether the direction is maintained, may be calculated.

Further, whether the dementia patient has a mobility disability is determined based on the speed and strength of motion at step S920.

Here, the state of the mobility disability may mean a situation in which it is inconvenient for the patient to move due to an accident, such as an injury from a fall.

When the speed and strength of motion are less than preset values, it may be determined that the dementia patient has a mobility disability.

Consequently, when it is determined that the dementia patient has a mobility disability, a helper service is activated at step S930.

Further, periodical motion speed and strength are analyzed and variations in the speed and strength are calculated at step S940. Variation in a periodic directionality decline is calculated based on the calculated values at step S950, and an integrated variation rate related to the motion symptoms of the patient is calculated at step S960.

Here, the periodic motion speed, strength, variations, etc. may be stored and managed for use by the dementia symptom recognition engine in predicting and recognizing dementia, as shown in FIG. 10.

FIG. 10 is an operation flowchart showing a procedure for recognizing the symptoms of dementia in the method for recognizing dementia and providing the dementia patient management service according to an embodiment of the present invention.

Referring to FIG. 10, dementia symptom recognition information is extracted using stored and managed information and sensed information at step S1010.

The dementia symptom recognition information may mean information about the degree of the decline in cognitive ability, the degree of the decline in memory, the degree of the decline in expressiveness, etc.

Further, a correlation and mutual influence between pieces of stored data are analyzed at step S1020.

Here, in order to analyze the mutual influence between the pieces of stored data, a dementia symptom recognition tree is constructed, and the influence of dementia symptoms may be analyzed using the dementia symptom recognition tree.

Further, the decline in cognitive ability, the decline in memory, the decline in expressiveness, and the environmental influence are analyzed at step S1030.

Next, variation in the decline in cognitive ability, variation in the decline in memory, variation in the decline in expressiveness, and the rates of variations thereof are calculated at step S1040.

In the case of the decline in cognitive ability, the declined state of cognitive ability is analyzed, and variation in a periodic cognitive ability decline or variation in a cognitive ability decline between a previous analysis time and a current analysis time may be calculated, and thus the rate of variation in the cognitive ability decline may be calculated.

Here, in the case of the memory decline, the declined state of memory may be analyzed, and variation in periodic memory decline or variation in memory decline between a previous analysis time and a current analysis time, and the rate of variation in memory decline may be calculated.

Further, in the case of the expressiveness decline, the declined state of expressiveness may be analyzed, and variation in periodic expressiveness decline or variation in expressiveness decline between a previous analysis time and a current analysis time, and the rate of variation in expressiveness decline may be calculated.

In the case of the environmental influence, the degree of the influence of the environment on dementia symptoms may be analyzed, and the frequency of occurrence of dementia symptoms depending on the environment in which the patient is located and the ambient environment of the patient, and the rate of variation in the dementia symptoms may be calculated.

Further, based on the rate of variation, the state of dementia is recognized, and the level of dementia symptoms is set at step S1050.

In this case, the states of signs and symptoms of dementia may be determined using information calculated through one or more of the cognitive ability analysis procedure, the memory analysis procedure, the expressiveness analysis procedure, and the environmental influence analysis procedure.

The levels of dementia symptoms may be chiefly classified into three levels, namely a high level, a middle level, and a low level.

Figure 11:
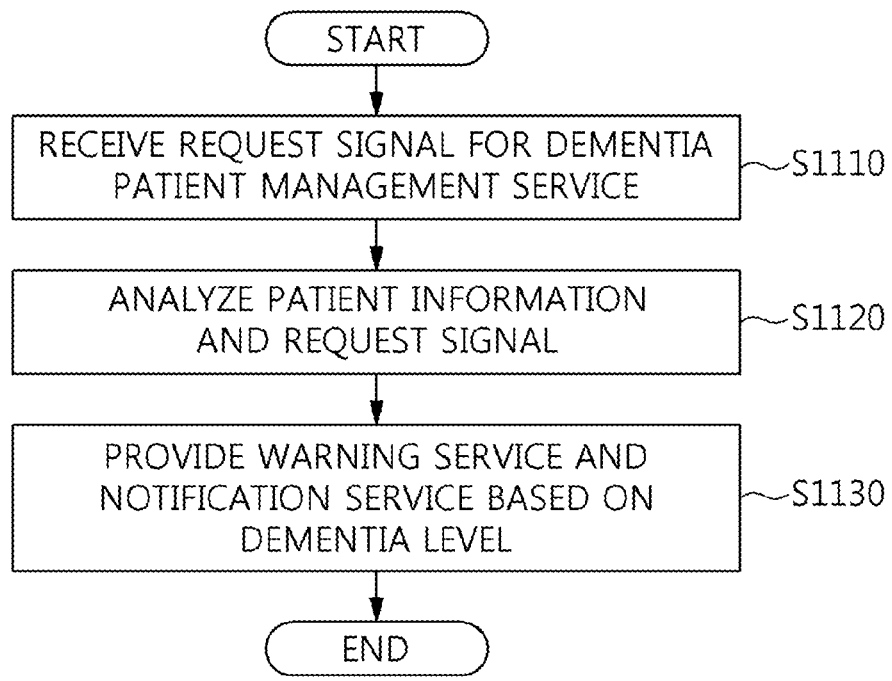
FIG. 11 is an operation flowchart showing a procedure for providing a dementia patient management service in the method for recognizing dementia and providing the dementia patient management service according to an embodiment of the present invention.

FIG. 11 is an operation flowchart showing a procedure for providing a dementia patient management service in the method for recognizing dementia and providing the dementia patient management service according to an embodiment of the present invention.

Referring to FIG. 11, a request signal for a dementia patient management service is received at step S1110.

Here, the request signal for the dementia patient management service means a signal for invoking the helper service described in FIG. 6, 7 or 9.

Further, information about the patient and the request signal from the patient are analyzed at step S1120.

The information about the patient may mean information including an ID corresponding to the patient, the location information of the patient, the dementia level of the patient, the gender and age of the patient, etc.

The request signal may include a management service request signal attributable to the occurrence of a physiological phenomenon. More specifically, this request signal may mean a signal for changing the diaper of the patient or purifying the ambient environment, which is contaminated by the physiological phenomenon of the patient when such a physiological phenomenon occurs.

In this case, the request signal may include a management service request signal in response to the deviation of the dementia patient from his or her designated location. For example, this request signal may correspond to a signal that includes a location deviation warning service request, which is required to track and monitor the location of the dementia patient from the house, building or outside area.

Here, the request signal may include a management service request signal related to the inconvenience in the movement of the dementia patient. For example, the cause of mobility difficulty of the dementia patient, such as an injury from a fall, may be analyzed, and the request signal may correspond to a request signal including the cause of the mobility difficulty of the patient, the location information of the patient, and the dementia level of the dementia patient.

Further, a warning service and a notification service are provided based on the level of dementia at step S1130. Step S1130 will be described in detail below with reference to FIG. 12.

Figure 12:
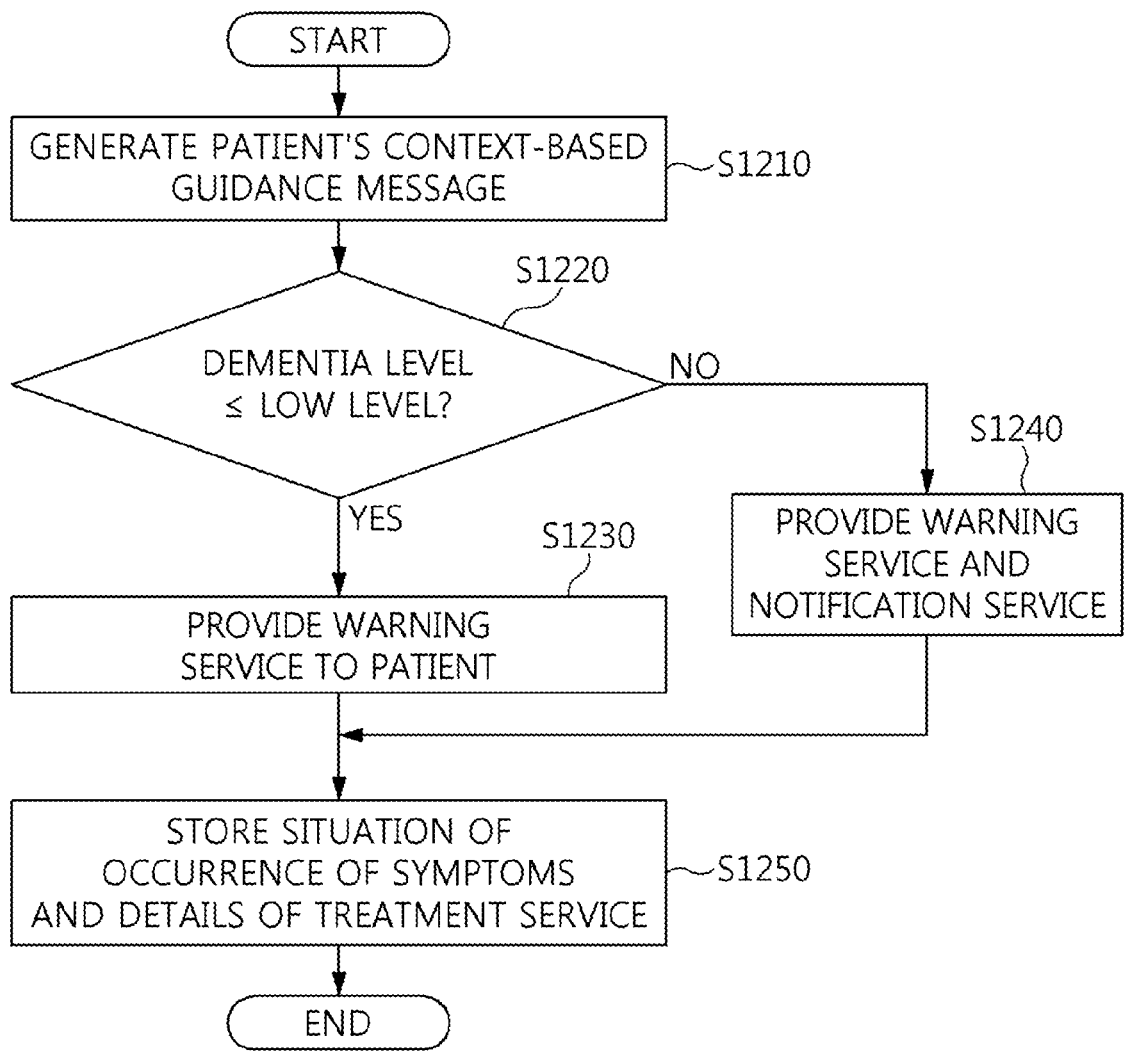
FIG. 12 is an operation flowchart showing a procedure for providing a warning service or a notification service depending on a dementia level in the method for recognizing dementia and providing the dementia patient management service according to an embodiment of the present invention.

FIG. 12 is an operation flowchart showing a warning service or a notification service depending on the dementia level in the method for recognizing dementia and providing the dementia patient management service according to an embodiment of the present invention.

Referring to FIG. 12, a context-based guidance message for the patient is generated at step S1210.

The context-based guidance message means a guidance message that includes patient information including one or more of the ID, location information, dementia level, gender, and age of the patient, and time and location information about the situation in which the patient is located (e.g. the occurrence of a physiological phenomenon, location deviation, or mobility difficulty).

Further, the level of dementia is analyzed, and whether the level of dementia is less than or equal to a low level is determined at step S1220.

In this case, when the level of dementia is less than or equal to the low level, a warning service may be provided to the patient at step S1230. That is, a notification service that is transmitted to the acquaintance or the like of the patient may not be provided.

Here, methods for providing the warning service to the patient are not especially limited. In an example, a method for displaying the warning service on the display of a device, such as a smart phone, owned by the patient may be used. In another example, a method for outputting a warning sound through the speaker of a device, such as a smart phone, owned by the patient may be used. Further, in a further example, a method for applying an effect such as a vibration to a device such as a smart phone, owned by the patient may be used.

For example, a warning service for indicating the occurrence and processing of a physiological phenomenon to the patient may be delivered. Further, in another example, a warning service indicating the deviation of the patient from the designated location and providing return guidance may be delivered to the patient. In a further example, a warning service indicating the occurrence of the mobility difficulty of the patient and guidance for the patient may be delivered to the patient.

Further, when the level of dementia is greater than the low level, that is, when the level of dementia corresponds to one of a middle level and a high level, a warning service may be provided to the patient and a notification service may be provided to the acquaintance of the patient at step S1240.

For example, when the patient has a physiological phenomenon, a physiological phenomenon occurrence message may be sent to the acquaintance or caretaker of the patient, and information about the method for treating such a physiological phenomenon may be provided. Further, for example, when the patient deviates from his or her designated location, a location deviation message may be sent to the acquaintance or caretaker of the patient, and a notification service including information about the time and place of the deviation may also be provided. Further, for example, when a patient has a mobility difficulty, a mobility difficulty message may be sent to the acquaintance or caretaker of the patient.

Here, the methods for providing a notification service to the acquaintance of the patient are not especially limited. For example, the notification service may be provided in such a way as to send a context-based guidance message to a device owned by the acquaintance of the patient in an SMS manner.

Further, the situation of occurrence of symptoms and service details for treating the symptoms are stored at step S1250.

The present invention may analyze signals measured using sensors for sensing dementia symptoms and may determine whether a patient is in an unconscious state and whether the patient correctly speaks words appropriate for a situation, thereby more conveniently recognizing dementia.

Further, the present invention may analyze signals measured using sensors, determine the situation in which a dementia patient is located, and send a message related to the situation in which the dementia patient is located to the patient and the acquaintance or caretaker of the patient while providing management service for the dementia patient appropriate for the situation, thus more efficiently protecting the dementia patient.

Furthermore, the present invention may provide differential management services for dementia patients depending on the dementia levels of dementia patients, thus more efficiently protecting dementia patients.

As described above, in the apparatus and method for detecting dementia and providing a dementia patient management service according to the present invention, the configurations and schemes in the above-described embodiments are not limitedly applied, and some or all of the above embodiments can be selectively combined and configured so that various modifications are possible.

What is claimed is:

1. An apparatus for recognizing dementia symptoms, comprising:
one or more processors that process computer executable program code embodied in non-transitory computer readable storage media, the computer executable program code comprising:
reception program code that receives physiological signals of a dementia patient collected by sensors corresponding to a dementia detection device, an ambient environmental information signal, a location signal, a motion signal, an audio signal, and a video signal corresponding to the dementia patient;
determination program code that analyzes the signals, and determines features of the dementia patient, wherein the features include information about whether the dementia patient is in an unconscious state during generation of the physiological signals and whether the patient correctly speaks words appropriate for a situation; and
symptom recognition program code that compares features corresponding to respective dementia symptoms with features of the dementia patient, determines variations in cognitive ability, memory, and expressiveness based on a result of the comparison, recognizes each dementia symptom based on the variations, and provides symptom recognition results to an apparatus for providing a dementia patient management service that provides a notification service to an acquaintance of the dementia patient,
wherein the physiological signals include indications of unintentional urination or unintentional defecation and such indications are used in predicting and recognizing dementia, and
wherein the determination program code determines whether a physiological phenomenon has occurred based on the physiological signals, and when the physiological phenomenon has occurred, determines that the dementia patient has a physiological phenomenon in an unconscious state if a management service request signal is not received or if a temperature physiological signal value and a humidity physiological signal value, which are measured after lapse of a preset period of time, fall within a specific range.

2. The apparatus of claim 1, wherein the symptom recognition program code sets a level of each dementia symptom based on a result of recognizing the dementia symptom.

3. The apparatus of claim 2, wherein the symptom recognition program code analyzes an association between the environmental information signal and the dementia symptom and determines a frequency of occurrence of the dementia symptom and a rate of variation in the dementia symptom depending on the ambient environment based on the association.

4. The apparatus of claim 3, wherein the symptom recognition program code determines rates of variation in the dementia symptom for respective time spans, rates of variation in the dementia symptom for respective temperatures, and rates of variation in the dementia symptom for respective humidity values.

5. The apparatus of claim 1, wherein:
the determination program code determines based on the location signal whether the patient has deviated from a designated location, and checks based on the location signal whether the patient has safely returned to the designated location when the patient has deviated from the designated location, and
the symptom recognition program code recognizes the dementia symptom based on a rate of increase in a number of unconscious deviations from the designated location when the rate of increase is equal to or greater than a specific value.

6. The apparatus of claim 5, wherein the symptom recognition program code receives family history information of the dementia patient, daily life information of the dementia patient, and medical examination information of the dementia patient, and recognizes the dementia symptom based on the received information and the variations in cognitive ability, memory, and expressiveness.

7. An apparatus for providing a dementia patient management service, comprising:
one or more processors that process computer executable program code embodied in non-transitory computer readable storage media, the computer executable program code comprising:
analysis program code that receives physiological signals of a dementia patient collected by sensors corresponding to a dementia detection device, an ambient environmental information signal, a location signal, a motion signal, an audio signal, and a video signal corresponding to the dementia patient, that analyzes the signals, and that analyzes a current condition of the dementia patient; and
service provision program code that provides a warning service corresponding to a specific situation and a notification service to an acquaintance of the dementia patient when it is determined, based on a result of a comparison between a preset condition of the dementia patient and the current condition of the dementia patient, that the current condition of the dementia patient indicates the specific situation,
wherein the physiological signals include indications of unintentional urination or unintentional defecation and such indications are used in predicting and recognizing dementia,
wherein the service provision program code that provides the notification service when a physiological phenomenon has occurred in an unconscious state, and
wherein the analysis program code that determines whether the physiological phenomenon has occurred based on the physiological signals, and when the physiological phenomenon has occurred, determines that the dementia patient has the physiological phenomenon in the unconscious state if a management service request signal is not sent or if a temperature physiological signal value and a humidity physiological signal value, which are measured after lapse of a preset period of time, fall within a specific range.

8. The apparatus of claim 7, wherein the service provision program code determines whether to provide the notification service based on a level of the dementia symptom.

9. The apparatus of claim 8, wherein the service provision program code provides both the warning service and the notification service when the level of the dementia symptom is any one of a high level and a middle level, and provides only a warning service when the level of the dementia symptom is a low level.

10. The apparatus of claim 9, wherein the service provision program code determines a location of the dementia patient based on the location signal, and provides the notification service to an acquaintance located closest to the dementia patient among registered acquaintances.

11. The apparatus of claim 10, wherein the service provision program code delivers a notification service including one or more of a physiological phenomenon and location information using a Short Message Service (SMS).

12. A method for recognizing dementia and providing a dementia patient management service, comprising:
processing computer executable program code embodied in non-transitory computer readable storage media by one or more processors, the computer executable program code comprising:
program code that receives physiological signals of a dementia patient collected by sensors corresponding to a dementia detection device, an ambient environmental information signal, a location signal, a motion signal, an audio signal, and a video signal corresponding to the dementia patient, that analyzes the signals, and that determines features of the dementia patient, wherein the features include information about whether the dementia patient is in an unconscious state during generation of the physiological signals and whether the patient correctly speaks words appropriate for a situation;
program code that analyzes features corresponding to respective dementia symptoms and the features of the dementia patient, that determines variations in cognitive ability, memory, and expressiveness based on a result of analysis, and that recognizes each dementia symptom based on the variations; and
program code that provides a warning service corresponding to a specific situation and a notification service to an acquaintance of the dementia patient when it is determined, based on a result of a comparison between a preset condition of the dementia patient and a current condition of the dementia patient, that the current condition of the dementia patient indicates a specific situation,
wherein the physiological signals include indications of unintentional urination or unintentional defecation and such indications are used in predicting and recognizing dementia, and
wherein the program code that recognizes each dementia symptom determines whether a physiological phenomenon has occurred based on the physiological signals, and when the physiological phenomenon has occurred, determines that the dementia patient has a physiological phenomenon in an unconscious state if a management service request signal is not received or if a temperature physiological signal value and a humidity physiological signal value, which are measured after lapse of a preset period of time, fall within a specific range.

13. The method of claim 12, wherein the program code that recognizes each dementia symptom sets a level of each dementia symptom based on a result of recognizing the dementia symptom.

14. The method of claim 13, wherein the program code that provides the notification service determines whether to provide the notification service based on the level of the dementia symptom.

15. The method of claim 14, wherein the program code that provides the notification service provides both the warning service and the notification service when the level of the dementia symptom is any one of a high level and a middle level, and provides only the warning service when the level of the dementia symptom is a low level.

16. The method of claim 15, wherein the program code that provides notification service delivers a notification service including one or more of a physiological phenomenon and location information using a Short Message Service (SMS).

17. The method of claim 13, wherein the program code that recognizes each dementia symptom analyzes an association between the environmental information signal and the dementia symptom and determines a frequency of occurrence of the dementia symptom and a rate of variation in the dementia symptom depending on the ambient environment based on the association.

18. The method of claim 12, wherein the program code that recognizes each dementia symptom receives family history information, daily life information, and medical examination information of the dementia patient, and recognizes the dementia symptom based on the received information and the variations in cognitive ability, memory, and expressiveness.

* * * * *